United States Patent
Beller et al.

(10) Patent No.: US 10,370,314 B2
(45) Date of Patent: Aug. 6, 2019

(54) SELECTIVE REDUCTION OF ESTERS TO ALCOHOLS

(71) Applicant: DSM IP ASSETS B.V., Heerlen (NL)

(72) Inventors: Matthias Beller, Rostock (DE); Werner Bonrath, Kaiseraugst (CH); Johannes Gerardus De Vries, Rostock (DE); Yuting Fan, Rostock (DE); Sandra Hinze, Rostock (DE); Laurent Lefort, Kaiseraugst (CH); Jonathan Alan Medlock, Kaiseraugst (CH); Pim Puylaert, Rostock (DE); Richard Van Heck, Rostock (DE)

(73) Assignee: DMS IP ASSETS B.V., Heerlen (NL)

( * ) Notice: Subject to any disclaimer, the term of this patent is extended or adjusted under 35 U.S.C. 154(b) by 0 days.

(21) Appl. No.: 16/300,269

(22) PCT Filed: May 11, 2017

(86) PCT No.: PCT/EP2017/061299
§ 371 (c)(1),
(2) Date: Nov. 9, 2018

(87) PCT Pub. No.: WO2017/194663
PCT Pub. Date: Nov. 16, 2017

(65) Prior Publication Data
US 2019/0144365 A1 May 16, 2019

(30) Foreign Application Priority Data

May 13, 2016 (EP) ..................................... 16169509
Jan. 23, 2017 (EP) ..................................... 17152592

(51) Int. Cl.
| | | |
|---|---|---|
| *B01J 31/18* | (2006.01) | |
| *B01J 31/22* | (2006.01) | |
| *B01J 31/24* | (2006.01) | |
| *C07C 33/14* | (2006.01) | |
| *C07C 33/22* | (2006.01) | |
| *C07C 33/32* | (2006.01) | |
| *C07C 29/149* | (2006.01) | |
| *C07C 31/125* | (2006.01) | |

(52) U.S. Cl.
CPC .......... *C07C 29/149* (2013.01); *B01J 31/181* (2013.01); *B01J 31/226* (2013.01); *B01J 31/24* (2013.01); *B01J 2531/0258* (2013.01); *B01J 2531/821* (2013.01); *C07C 31/125* (2013.01); *C07C 33/14* (2013.01); *C07C 33/22* (2013.01); *C07C 33/32* (2013.01)

(58) Field of Classification Search
CPC ..... C07C 29/149; C07C 33/22; C07C 31/125; C07C 2601/16; C07C 33/32; C07C 31/20; C07C 33/14; B01J 31/0212; B01J 31/1805; B01J 31/226; B01J 31/24; B01J 31/2404; B01J 2231/643; B01J 2531/0258; B01J 2531/825; B01J 2531/842; B01J 2531/845
See application file for complete search history.

(56) References Cited

PUBLICATIONS

Sujan Biswas, et al., "Rhodium(III)-triphenylphosphine complex with NNS donor thioether containing Schiff base ligand: Synthesis, spectra, electrochemistry and catalytic activity", Journal of Molecular Structure, Jun. 29, 2015, vol. 1099, pp. 297-303. (7 pages).
Svenja Werkmeister, et al., "Catalytic Hydrogenation of Carboxylic Acid Esters, Amides, and Nitriles with Homogeneous Catalysts", Organic Process Research & Development, Jan. 13, 2014, vol. 18, No. 2, pp. 289-302. (14 pages).
International Search Report for PCT/EP2017/061299 dated Jul. 17, 2017. (2 pages).
Written Opinion of the ISA for PCT/EP2017/061299 dated Jul. 17, 2017. (5 pages).

*Primary Examiner* — Jafar F Parsa
(74) *Attorney, Agent, or Firm* — Nixon & Vanderhye P.C.

(57) ABSTRACT

The present invention relates to a selective reduction of esters to their corresponding alcohols.

12 Claims, No Drawings

SELECTIVE REDUCTION OF ESTERS TO ALCOHOLS

This application is the U.S. national phase of International Application No. PCT/EP2017/061299 filed May 11, 2017 which designated the U.S. and claims priorities to EP 16169509.3 filed May 13, 2016, and EP 17152592.6 filed Jan. 23, 2017, the entire contents of each of which are hereby incorporated by reference.

The present invention relates to a selective reduction of esters to their corresponding alcohols.

Reduction of an ester into the corresponding alcohol is a fundamental and very important reaction in organic chemistry, and is used in a large number of chemical processes. The obtained alcohols are used as such or are important intermediates in further chemical processes.

To reduce such esters, usually harsh reaction conditions have to be applied.

Furthermore, the reduction of esters usually requests the use of highly reactive reducing agents such as $LiAlH_4$ or $NaBH_4$, which are not easy to handle and which produce a lot waste as a result of the reaction.

The esters which are reduced in the context of the present invention are esters of formula (I)

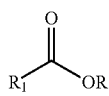

(I)

wherein R is a linear $C_1$-$C_6$-alkyl group, which can be substituted; a branched $C_3$-$C_6$-alkyl group, which can be substituted or a benzyl group, which can be substituted, and $R_1$ can be a suitable organic moiety (which is defined below).

The goal of the present invention was to provide a process for the improved production of the following compounds of formula (II)

(II)

As stated above the esters, which are of interest in the context of the present patent application are those of formula (I)

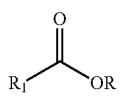

(I)

wherein

R is a linear $C_1$-$C_6$-alkyl group, which can be substituted; a branched $C_3$-$C_6$-alkyl group, which can be substituted or a benzyl group, which can be substituted, and $R_1$ is an aromatic ring system which is unsubstituted (such as a benzene ring) or an aromatic ring system which is substituted; a heteroaromatic ring system which is unsubstituted or a heteroaromatic ring system which is substituted; an aliphatic ring system which is unsubstituted or an aliphatic ring system which is substituted; —$CH_3$; —$CH_2CH_3$; an unsubstituted $C_3$-$C_{22}$ alkyl group, which can be linear or branched and which can also be partially unsaturated (comprising C—C double bond(s)); or an substituted $C_2$-$C_{22}$ alkyl group, which can be linear or branched and which can also be partially unsaturated, or R and $R_1$ form together a 4 to 7 membered ring system, which can be substituted.

The corresponding alcohols, which are the selectively hydrogenated products are those of formula (II)

(II)

wherein the substituent $R_1$ has the same definition as in formula (I).

Surprisingly it was found that by the use of new specific catalysts, it is possible to selectively reduce the compounds of formula (I) in excellent yield and selectivity under mild reaction conditions.

The catalysts, which are used in the selective reduction (hydrogenation) according to the present invention are transition metal catalysts of formula (III)

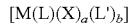

$[M(L)(X)_a(L')_b]$  (III), wherein

M is a transition metal (preferably a transition metal chosen from the group consisting of Os, Co, Ru and Fe, more preferably from the group consisting of Ru and Fe) and X is an anion (preferably a halogen anion, a carboxylate (such as acetate or benzoate), borohydride (such as $BH_4^-$), hydride, $BF_4^-$, or $PF_6^-$, more preferably a halogen anion, most preferably $Cl^-$), and L' is a monodentate ligand (preferably a monodentate phosphine ligand, more preferably triphenylphosphine (=$PPh_3$)), and L is a tridentate ligand (which means that the ligand can be bound to the M at up to three sites) of formula (IV)

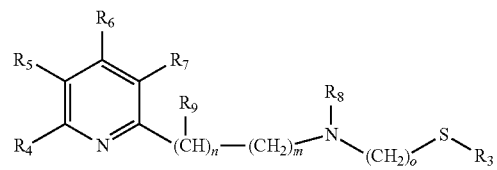

(IV)

wherein $R_3$ is a linear $C_1$-$C_4$ alkyl group, which can be substituted; a branched $C_3$-$C_4$ alkyl group, which can be substituted; or a phenyl group, which can be substituted, and $R_4$ is H; a linear $C_1$-$C_4$ alkyl group, which can be substituted; a branched $C_3$-$C_4$ alkyl group, which can be substituted; or $OC_1$-$C_2$alkyl, and $R_5$ is H; a linear $C_1$-$C_4$ alkyl group, which can be substituted; a branched $C_3$-$C_4$ alkyl group, which can be substituted; or $OC_1$-$C_2$alkyl, or $R_4$ and $R_5$ form a $C_4$-$C_8$ ring system, which can be aliphatic or aromatic, and $R_6$ is H; a linear $C_1$-$C_4$ alkyl group, which can be substituted; a branched $C_3$-$C_4$ alkyl group, which can be substituted; or $OC_1$-$C_2$alkyl, and $R_7$ is H; a linear $C_1$-$C_4$ alkyl group, which can be substituted; a branched $C_3$-$C_4$ alkyl group, which can be substituted; or $OC_1$-$C_2$alkyl, and $R_8$ is H or a linear $C_1$-$C_4$ alkyl group, which can be substituted; a branched $C_3$-$C_4$ alkyl group, which can be substituted, and $R_9$ is —$CH_3$ or —$CH_2CH_3$, and m is 0, 1 or 2, and n is 0, 1 or 2, with the proviso that the sum of m+n is 1 or 2, o is 2 or 3, a is 0, 1, 2, or 3, b is 0, 1, 2, or 3, with the proviso that the sum of a+b is 2, 3 or 4.

From the state of the art, it is known that transition metal complexes can exist as monomers as well as dimers or even oligomers. The present formula (III) defines the empirical formula of the catalyst.

Therefore the present invention relates to a process (P) of production of a compound of formula (II)

(II)

wherein $R_1$ is an aromatic ring system which is unsubstituted (such as a benzene ring) or an aromatic ring system which is substituted; a heteroaromatic ring system which is unsubstituted or a heteroaromatic ring system which is substituted; an aliphatic ring system which is unsubstituted or an aliphatic ring system which is substituted; —$CH_3$; —$CH_2CH_3$; an unsubstituted $C_3$-$C_{22}$ alkyl group, which can be linear or branched and which can also be partially unsaturated (comprising C—C double bond(s)); or an substituted $C_2$-$C_{22}$ alkyl group, which can be linear or branched and which can also be partially unsaturated by a selective reduction of a compound of formula (I)

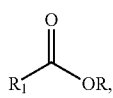
(I)

wherein

R is a linear $C_1$-$C_6$-alkyl group, which can be substituted; a branched $C_3$-$C_6$-alkyl group, which can be substituted or a benzyl group, which can be substituted, and $R_1$ is an aromatic ring system which is unsubstituted (such as a benzene ring) or an aromatic ring system which is substituted; a heteroaromatic ring system which is unsubstituted or a heteroaromatic ring system which is substituted; an aliphatic ring system which is unsubstituted or an aliphatic ring system which is substituted; —$CH_3$; —$CH_2CH_3$; an unsubstituted $C_3$-$C_{22}$ alkyl group, which can be linear or branched and which can also be partially unsaturated (comprising C—C double bond(s)); or an substituted $C_2$-$C_{22}$ alkyl group, which can be linear or branched and which can also be partially unsaturated, or R and $R_1$ form together a 4 to 7 membered ring system, which can be substituted, characterised in that the selective reduction is carried out in the presence of at least one transition metal catalyst of formula (III)

$$[M(L)(X)_a(L')_b] \quad (III),$$

wherein

M is a transition metal and

X is an anion, and

L' is a monodentate ligand, and

L is a tridentate ligand of formula (IV)

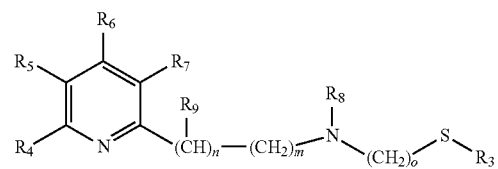

wherein $R_3$ is a linear $C_1$-$C_4$ alkyl group, which can be substituted; a branched $C_3$-$C_4$ alkyl group, which can be substituted; or a phenyl group, which can be substituted, and $R_4$ is H; a linear $C_1$-$C_4$ alkyl group, which can be substituted; a branched $C_3$-$C_4$ alkyl group, which can be substituted; or $OC_1$-$C_2$alkyl, and $R_5$ is H; a linear $C_1$-$C_4$ alkyl group, which can be substituted; a branched $C_3$-$C_4$ alkyl group, which can be substituted; or $OC_1$-$C_2$alkyl, or $R_4$ and $R_5$ form a $C_4$-$C_8$ ring system, which can be aliphatic or aromatic, and $R_6$ is H; a linear $C_1$-$C_4$ alkyl group, which can be substituted; a branched $C_3$-$C_4$ alkyl group, which can be substituted; or $OC_1$-$C_2$alkyl, and $R_7$ is H; a linear $C_1$-$C_4$ alkyl group, which can be substituted; a branched $C_3$-$C_4$ alkyl group, which can be substituted; or $OC_1$-$C_2$alkyl, and $R_8$ is H or a linear $C_1$-$C_4$ alkyl group, which can be substituted; a branched $C_3$-$C_4$ alkyl group, which can be substituted, and $R_9$ is —$CH_3$ or —$CH_2CH_3$, and m is 0, 1 or 2, and n is 0, 1 or 2, with the proviso that the sum of m+n is 1 or 2, o is 2 or 3, a is 0, 1, 2, or 3, b is 0, 1, 2, or 3, with the proviso that the sum of a+b is 2, 3 or 4.

The process according to the present invention is preferably carried out in the presence of at least one base.

Preferably the base has the following formula (VIII)

$$M^1(OC_1\text{-}C_5\text{alkyl}) \quad (VIII),$$

wherein $M^1$ is an alkali metal.

Preferred is a base of formula (VIII'), $$M^1(OC_3\text{-}C_5\text{alkyl}) \quad (VIII')$$

wherein $M^1$ is Li, Na or K.

Especially preferred bases are selected from the group consisting of KOtBu, NaOtBu and LiOtBu.

Therefore the present invention relates to a process (P1), which is process (P), wherein the process is carried out in the presence of at least one base.

Therefore the present invention relates to a process (P1'), which is process (P1), wherein the process is carried out in the presence of at least one base of formula (VIII)

$M^1(OC_1\text{-}C_5\text{alkyl})$ (VIII)

wherein $M^1$ is an alkali metal.

Therefore the present invention relates to a process (P1″), which is process (P1), wherein the process is carried out in the presence of at least one base of formula (VIII'),

$M^1(OC_3\text{-}C_5\text{alkyl})$ (VIII')

wherein
$M^1$ is Li, Na or K.

Therefore the present invention relates to a process (P1‴), which is process (P1), wherein the process is carried out in the presence of at least one base selected from the group consisting of KOtBu, NaOtBu and LiOtBu.

The amount of the base can vary. Usually and preferably the base (or mixture of bases) is used in an amount of 0.1-5 mol-% (based on the number of moles of the compound of formula (I)).

Therefore the present invention relates to a process (P1″″), which is process (P1), (P1'), (P1″) or (P1‴), wherein 0.1-5 mol-% (based on the number of moles of the compound of formula (I)) of at least one base is used.

The catalyst of the present invention which is used to selectively reduce the compound of formula (I) is a compound of formula (III) as defined above.

In a preferred embodiment the following catalysts are used:

$[M(L)(X)_a(L')_b]$ (III), wherein
M is a transition metal chosen from the group consisting of Os, Co, Ru and Fe, and
X is a halogen anion, a carboxylate (such as acetate or benzoate), borohydride (such as $BH_4^-$), hydride, $BF_4^-$ or $PF_6^-$, and
L' is a monodentate phosphine ligand, and
L is a tridentate ligand of formula (IV)

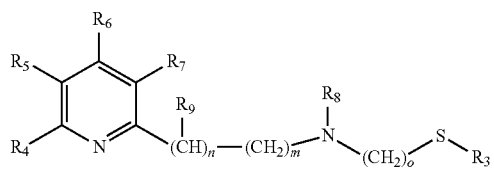

(IV)

wherein
$R_3$ is —$CH_3$ or —$CH_2CH_3$, and
$R_4$ is H; —$CH_3$; —$CH_2CH_3$; —$OCH_3$ or —$OCH_2CH_3$, and
$R_5$ is H; —$CH_3$; —$CH_2CH_3$; —$OCH_3$ or —$OCH_2CH_3$,
or $R_4$ and $R_5$ form a $C_4$-$C_8$ ring system, which can be aliphatic or aromatic, and
$R_6$ is H; —$CH_3$; —$CH_2CH_3$; —$OCH_3$ or —$OCH_2CH_3$, and
$R_7$ is H; —$CH_3$; —$CH_2CH_3$; —$OCH_3$ or —$OCH_2CH_3$, and
$R_8$ is H; —$CH_3$ or —$CH_2CH_3$, and
$R_9$ is —$CH_3$ or —$CH_2CH_3$, and
m is 0, 1 or 2, and
n is 0, 1 or 2,
with the proviso that the sum of m+n is 1 or 2,
o is 2 or 3,
a is 0, 1, 2, or 3,
b is 0, 1, 2, or 3,
with the proviso that the sum of a+b is 2 or 3.

In a more preferred embodiment the following catalysts are used:

$[M(L)(X)_a(L')_b]$ (III), wherein
M is a transition metal chosen from the group consisting of Ru and Fe, and
X is a halogen anion (preferably Cl⁻), and
L' is triphenylphosphine, and
L is a tridentate ligand of formula (IV)

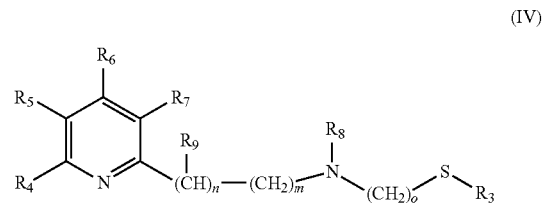

(IV)

wherein
$R_3$ is —$CH_3$ or —$CH_2CH_3$, and
$R_4$ is H; —$CH_3$; —$CH_2CH_3$; —$OCH_3$ or —$OCH_2CH_3$, and
$R_5$ is H or —$CH_3$,
or $R_4$ and $R_5$ form a $C_4$-$C_8$ ring system, which can be aliphatic or aromatic, and
$R_6$ is H or —$CH_3$, and
$R_7$ is H or —$CH_3$, and
$R_8$ is H or —$CH_3$, and
$R_9$ is —$CH_3$, and
m is 0 or 1 and
n is 0 or 1,
with the proviso that the sum of m+n is 1,
o is 2,
a is 1 or 2,
b is 1 or 2,
with the proviso that the sum of a+b is 3.

In an especially preferred embodiment the following catalysts of formula (III')

$M(L)(X)_2(L')$ (III'), wherein
M is Ru or Fe, and
X is Cl⁻, and
L' is $PPh_3$, and
L is a tridentate ligand chosen from the group consisting of the ligands of formulae (IVa)-(IVl)

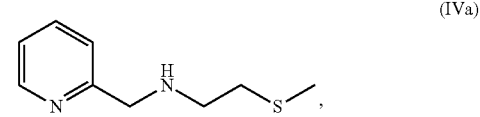

(IVa)

(IVb)

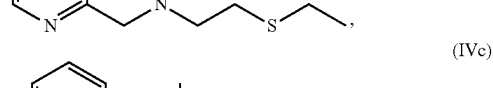

(IVc)

-continued (IVd) 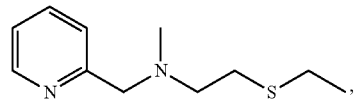

(IVe) 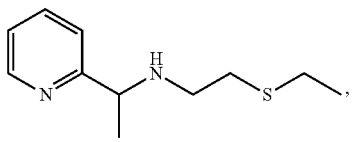

(IVf) 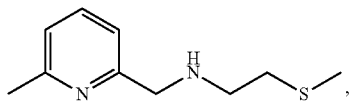

(IVg) 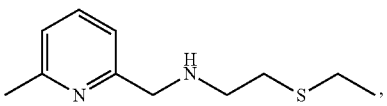

(IVh) 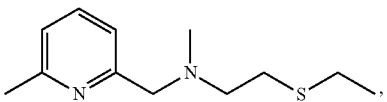

(IVi) 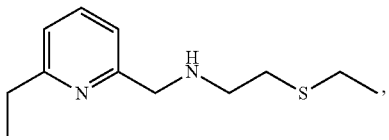

(IVj) 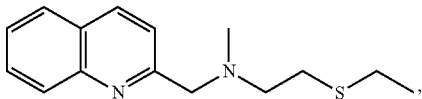

(IVk) 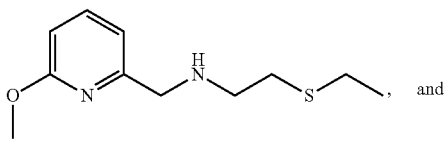, and (IVl) 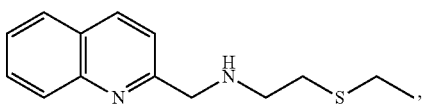

are used.

Therefore the present invention relates to a process (P2), which is process (P), (P1), (P1'), (P1''), (P1''') or (P1''''), wherein the following catalysts of formula (III)

[M(L)(X)$_a$(L')$_b$]     (III), wherein

M is a transition metal chosen from the group consisting of Os, Co, Ru and Fe, and X is a halogen anion, a carboxylate (such as acetate or benzoate), borohydride (such as BH$_4^-$), hydride, BF$_4^-$ or PF$_6^-$, and L' is a monodentate phosphine ligand, and
L is a tridentate ligand of formula (IV)

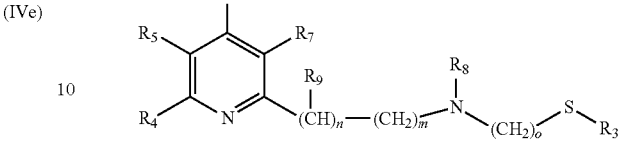     (IV)

wherein
R$_3$ is —CH$_3$ or —CH$_2$CH$_3$, and
R$_4$ is H; —CH$_3$; —CH$_2$CH$_3$; —OCH$_3$ or —OCH$_2$CH$_3$, and
R$_5$ is H; —CH$_3$; —CH$_2$CH$_3$; —OCH$_3$ or —OCH$_2$CH$_3$,
or R$_4$ and R$_5$ form a C$_4$-C$_8$ ring system, which can be aliphatic or aromatic, and
R$_6$ is H; —CH$_3$; —CH$_2$CH$_3$; —OCH$_3$ or —OCH$_2$CH$_3$, and
R$_7$ is H; —CH$_3$; —CH$_2$CH$_3$; —OCH$_3$ or —OCH$_2$CH$_3$, and
R$_8$ is H; —CH$_3$ or —CH$_2$CH$_3$, and
R$_9$ is —CH$_3$ or —CH$_2$CH$_3$, and
m is 0, 1 or 2, and
n is 0, 1 or 2,
with the proviso that the sum of m+n is 1 or 2,
o is 2 or 3,
a is 0, 1, 2, or 3,
b is 0, 1, 2, or 3,
with the proviso that the sum of a+b is 2 or 3,
are used.

Therefore the present invention relates to a process (P2'), which is process (P), (P1), (P1'), (P1''), (P1''') or (P1''''), wherein the following catalysts of formula (III)

[M(L)(X)$_a$(L')$_b$]     (III),

M is a transition metal chosen from the group consisting of Ru and Fe, and
X is a halogen anion (preferably Cl$^-$), and
L' is triphenylphosphine, and
L is a tridentate ligand of formula (IV)

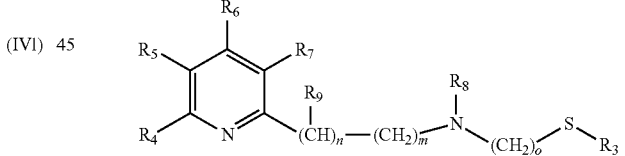     (IV)

wherein
R$_3$ is —CH$_3$ or —CH$_2$CH$_3$, and
R$_4$ is H; —CH$_3$; —CH$_2$CH$_3$; —OCH$_3$ or —OCH$_2$CH$_3$, and
R$_5$ is H or —CH$_3$, and
or R$_4$ and R$_5$ form a C$_4$-C$_8$ ring system, which can be aliphatic or aromatic, and
R$_6$ is H or —CH$_3$, and
R$_7$ is H or —CH$_3$, and
R$_8$ is H or —CH$_3$, and
R$_9$ is —CH$_3$, and
m is 0 or 1, and
n is 0 or 1,
with the proviso that the sum of m+n is 1,
o is 2,
a is 1 or 2,
b is 1 or 2,
with the proviso that the sum of a+b is 3,
are used.

Therefore the present invention relates to a process (P2"), which is process (P), (P1), (P1'), (P1"), (P1'") or (P1""), wherein the following catalysts of formula (III')

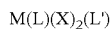 (III'), wherein

M is Ru or Fe, and

X is Cl⁻, and

L' is PPh₃, and

L is a tridentate ligand chosen from the group consisting of the ligands of formulae (IVa)-(IVl)

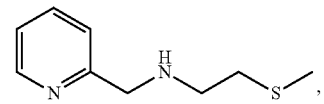 (IVa)

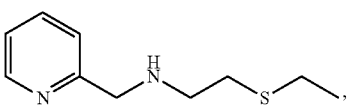 (IVb)

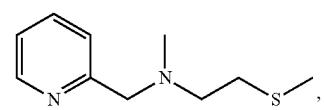 (IVc)

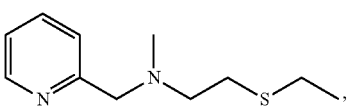 (IVd)

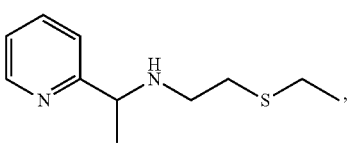 (IVe)

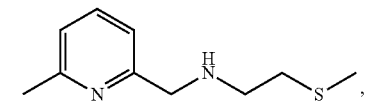 (IVf)

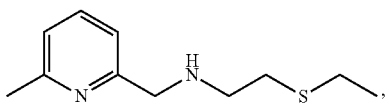 (IVg)

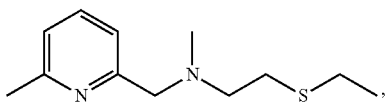 (IVh)

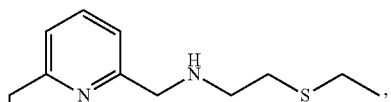 (IVi)

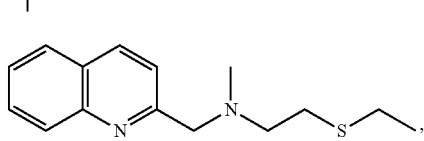 (IVj)

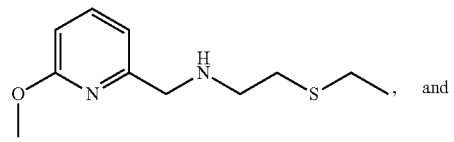 (IVk)

and

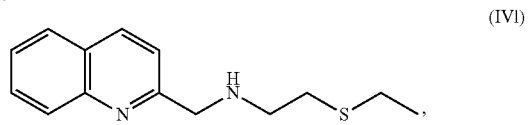 (IVl)

are used.

The catalysts of the present invention are also new. The synthesis of the catalyst are described in details below.

Preferred embodiments of the present invention relate to selective reductions of the following compounds of formula (I)

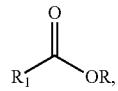 (I)

R is a linear $C_1$-$C_4$-alkyl group, which can be substituted; a branched $C_3$-$C_6$-alkyl group, which can be substituted or a benzyl group, which can be substituted $R_1$ is an unsubstituted benzene ring or benzene ring which is substituted; a heteroaromatic ring system which is unsubstituted or a heteroaromatic ring system which is substituted; an aliphatic ring system which is unsubstituted or an aliphatic ring system which is substituted; —CH₃; —CH₂CH₃; an unsubstituted $C_2$-$C_{22}$ alkyl group, which can be linear or branched and which can also be partially unsaturated or a substituted $C_2$-$C_{22}$ alkyl group, which can be linear or branched and which can also be partially unsaturated, or R and $R_1$ form together a 4 to 7 membered ring system, which can be substituted.

More preferred embodiments of the present invention relate to selective reductions of the following compounds of formula (I)

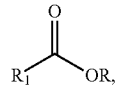 (I)

R is a linear $C_1$-$C_4$-alkyl group, which can be substituted or a branched $C_3$-$C_6$-alkyl group, which can be substituted $R_1$ is an unsubstituted benzene ring or benzene ring, which is substituted; a heteroaromatic ring system which is unsubstituted or a heteroaromatic ring system which is substituted; an aliphatic ring system which is unsubstituted; an aliphatic ring system which is substituted or a substituted $C_2$-$C_{10}$ alkyl group, which can be linear or branched and which can also be partially unsaturated or a substituted $C_2$-$C_{10}$ alkyl group which can also be partially unsaturated, or R and $R_1$ form together a 4 to 7 membered ring system, which can be substituted Especially preferred embodiments of the present invention relate to selective reductions of the following compounds of formula (Ia) to (If)

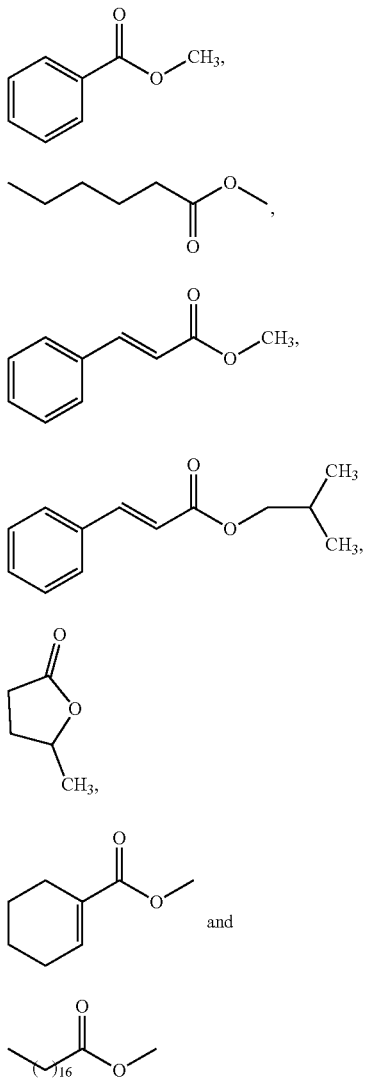

The following compounds of formulae (IIa) to (IIf) are the corresponding ones to the starting material (compounds of formula (Ia) to (If). The compounds of formula (Ic) and (Ic') do react to the same compound of formula (IIc):

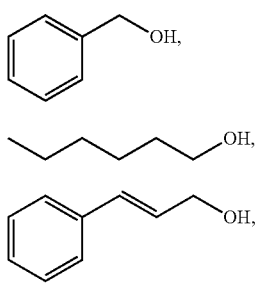

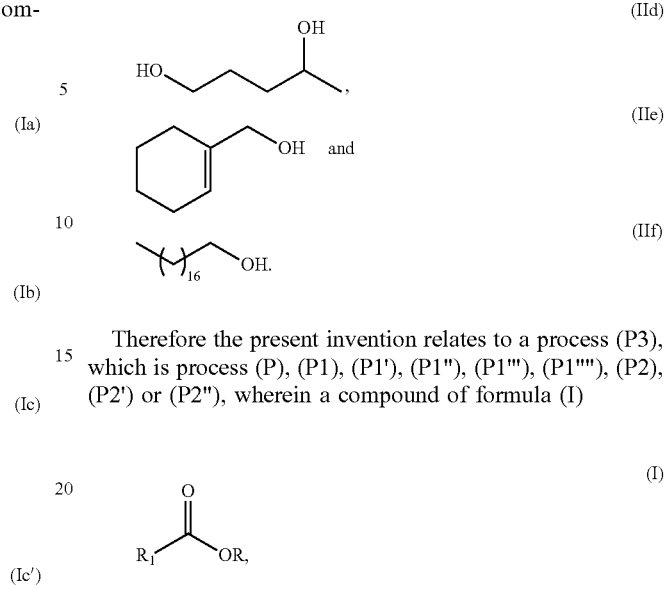

Therefore the present invention relates to a process (P3), which is process (P), (P1), (P1'), (P1"), (P1'"), (P1""), (P2), (P2') or (P2"), wherein a compound of formula (I)

R is a linear $C_1$-$C_4$-alkyl group, which can be substituted; a branched $C_3$-$C_6$-alkyl group, which can be substituted or a benzyl group, which can be substituted $R_1$ is an unsubstituted benzene ring or benzene ring which is substituted; a heteroaromatic ring system which is unsubstituted or a heteroaromatic ring system which is substituted; an aliphatic ring system which is unsubstituted or an aliphatic ring system which is substituted; —$CH_3$; —$CH_2CH_3$; an unsubstituted $C_2$-$C_{22}$ alkyl group, which can be linear or branched and which can also be partially unsaturated or a substituted $C_2$-$C_{22}$ alkyl group, which can be linear or branched and which can also be partially unsaturated, or R and $R_1$ form together a 4 to 7 membered ring system, which can be substituted, is selectively reduced.

Therefore the present invention relates to a process (P3'), which is process (P), (P1), (P1'), (P1"), (P1'"), (P1""), (P2), (P2') or (P2"), wherein a compound of formula (I)

$$R_1 \overset{O}{\underset{}{\diagdown}} OR,$$ (I)

R is a linear $C_1$-$C_4$-alkyl group, which can be substituted or a branched $C_3$-$C_6$-alkyl group, which can be substituted $R_1$ is an unsubstituted benzene ring or benzene ring, which is substituted; a heteroaromatic ring system which is unsubstituted or a heteroaromatic ring system which is substituted; an aliphatic ring system which is unsubstituted; an aliphatic ring system which is substituted or a substituted $C_2$-$C_{10}$ alkyl group, which can be linear or branched and which can also be partially unsaturated or a substituted $C_2$-$C_{10}$ alkyl group which can also be partially unsaturated, is selectively reduced.

Therefore the present invention relates to a process (P3"), which is process (P), (P1), (P1'), (P1"), (P1'"), (P1""), (P2), (P2') or (P2"), wherein a compound chosen from the group consisting of the following compounds

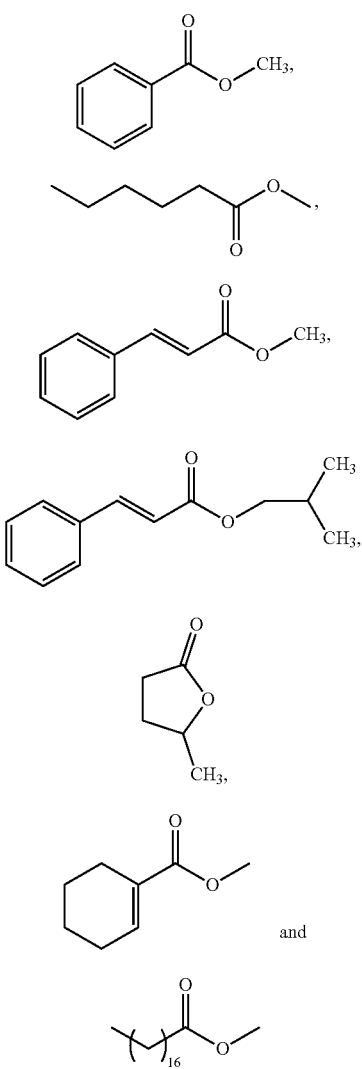

is selectively reduced.

In the following the synthesis of the catalyst used in the selective reduction of the present invention is described.

Production of the Ligand L (Compounds of Formula (IV))

The ligand (L) is usually made first and this ligand (L) is then used afterwards to synthesise the transition metal based catalyst of formula (III).

The production of the ligands (wherein $R_8$ is H) is usually done by the following reaction scheme (RS):

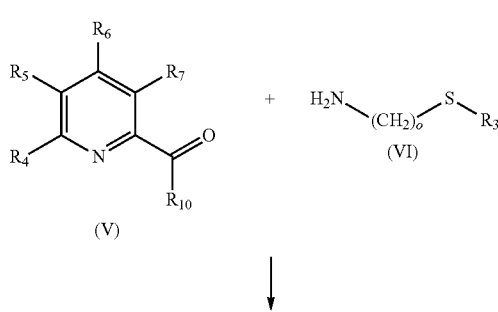

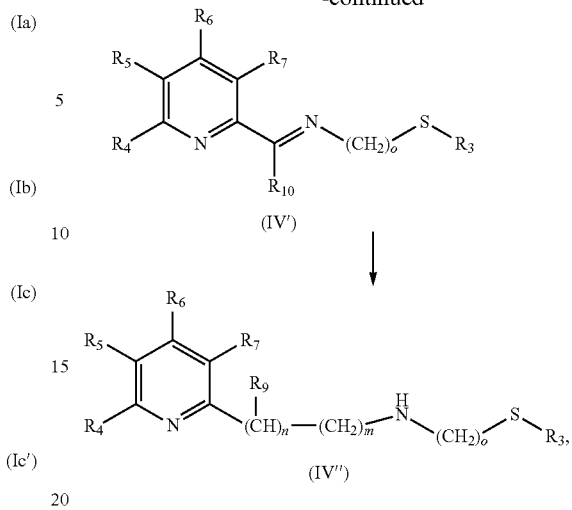

wherein $R_{10}$ is H or has the same meaning as $R_9$, all other substituents and letters have the meanings as defined above.

To obtain the ligands (wherein $R_8$ is —CH$_3$ or —CH$_2$CH$_3$), the process of RS is carried out and then in an additional step the amino group is alkylated.

The process of the production of the ligand is usually carried out in a solvent (or a mixture of solvents).

Suitable solvents are esters, ethers, amides, hydrocarbons, halogenated hydrocarbons and alcohols. Preferred solvents are CH$_2$Cl$_2$, toluene, ethyl acetate, THF, methanol and ethanol.

The process of the production of the ligand is usually carried out at temperature of between 0 and 120° C. (preferably 0-40° C.).

The process of the production of the ligand is usually carried at ambient pressure.

The obtained ligand of formula (IV″) (with $R_8$=H) is removed from the reaction mixture by extraction and can be further purified if required. The yield is very good.

To obtain the ligands of formula (IV) wherein $R_8$ is CH$_3$ or CH$_2$CH$_3$, the obtained ligand of formula (IV″) is alkylated in an additional step.

This alkylation step can be carried out according to commonly known processes.

Production of the Catalyst (Compounds of Formula (III))

As stated above the catalysts of the present invention are new.

They are produced by commonly known processes. Usually (and preferably in the context of the present invention) they are produced as follows (reaction scheme (RS2)):

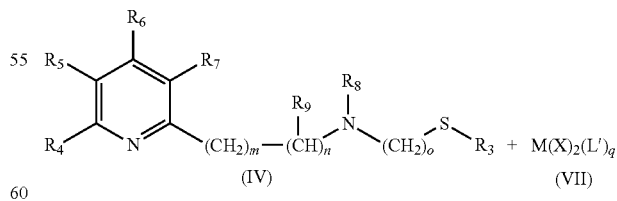

wherein q is 1, 2 or 3 and
all other substituents have the meanings as defined above.

The process to obtain the catalyst (RS2) is usually carried out in a solvent (or a mixture of solvents). Suitable solvents are esters, ethers, amides, hydrocarbons, and alcohols. Preferred solvents are toluene, ethyl acetate, THF and diglyme.

The process to obtain the catalyst is usually carried out at elevated temperature (50-180°).

The process to obtain the catalyst is usually carried out at ambient pressure

The obtained catalyst (in crystalline form) are filtered off and they can be further purified.

As stated above the obtained catalysts are used in the selective reductions (selective hydrogenations), wherein the yield and selectivity of the desired product is excellent.

Reduction Process

The reduction process (selective hydrogenation) of the compound of formula (I) can be carried out according to the following reaction scheme

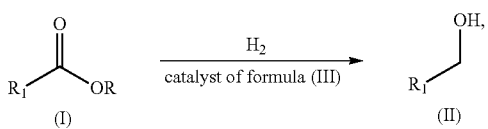

wherein all substituents have meanings as defined above.

In these hydrogenation processes $H_2$ is added in form of a gas (pure $H_2$ gas or part of a mixture).

The catalyst of formula (III) according to the present invention is usually used in an amount of 0.001-0.5 mol-% (based on the number of moles of the compounds of formula (I)).

Therefore the present invention relates to a process (P4), which is process (P), (P1), (P1'), (P1"), (P1'''), (P1''''), (P2), (P2'), (P2"), (P3), (P3') or (P3"), wherein the at least one catalyst of formula (III) is used in an amount of 0.001-0.5 mol-% (based on the number of moles of the compounds of formula (I)).

The hydrogenation process can be carried out with (pure) $H_2$ gas or with a gas which comprises $H_2$. Preferably the hydrogenation process according to the present invention is carried out with (pure) $H_2$ gas.

Therefore the present invention relates to a process (P5), which is process (P), (P1), (P1'), (P1"), (P1'''), (P1''''), (P2), (P2'), (P2"), (P3), (P3'), (P3") or (P4), wherein the hydrogenation is carried out with (pure) $H_2$ gas or with a gas which comprises $H_2$. Preferably the hydrogenation process according to the present invention is carried out with (pure) $H_2$ gas.

Therefore the present invention relates to a process (P5'), which is process (P), (P1), (P1'), (P1"), (P1'''), (P1''''), (P2), (P2'), (P2"), (P3), (P3'), (P3") or (P4), wherein the hydrogenation is carried out with pure $H_2$ gas.

The hydrogenation process can be carried out at ambient pressure as well as at elevated pressure. Preferably the hydrogenation process according to the present invention is carried out at elevated pressure (10-50 bar), usually in an autoclave (or any other vessel, which can resist the pressure.

Therefore the present invention relates to a process (P6), which is process (P), (P1), (P1'), (P1"), (P1'''), (P1''''), (P2), (P2'), (P2"), (P3), (P3'), (P3"), (P4), (P5) or (P5'), wherein the hydrogenation is carried out at ambient pressure.

Therefore the present invention relates to a process (P6'), which is process (P), (P1), (P1'), (P1"), (P1'''), (P1''''), (P2), (P2'), (P2"), (P3), (P3'), (P3"), (P4), (P5) or (P5'), wherein the hydrogenation is carried out at elevated pressure (10-50 bar).

The hydrogenation can be carried out in a solvent (or mixture of solvents). Suitable solvents are esters, ethers, amides, hydrocarbons, halogenated hydrocarbons and alcohols. Preferred solvents are $CH_2Cl_2$, toluene, ethyl acetate, THF, methanol, ethanol and isopropanol, especially preferred solvents are toluene and isopropanol.

Therefore the present invention relates to a process (P7), which is process (P), (P1), (P1'), (P1"), (P1'''), (P1''''), (P2), (P2'), (P2"), (P3), (P3'), (P3"), (P4), (P5), (P5'), (P6) or (P6'), wherein the hydrogenation is carried out carried out in at least one solvent.

Therefore the present invention relates to a process (P7'), which is process (P), (P1), (P1'), (P1"), (P1'''), (P1''''), (P2), (P2'), (P2"), (P3), (P3'), (P3"), (P4), (P5), (P5'), (P6) or (P6'), wherein the hydrogenation is carried out carried out in at least one solvent chosen from the group consisting of esters, ethers, amides, hydrocarbons, halogenated hydrocarbons and alcohols.

Therefore the present invention relates to a process (P7"), which is process (P), (P1), (P1'), (P1"), (P1'''), (P1''''), (P2), (P2'), (P2"), (P3), (P3'), (P3"), (P4), (P5), (P5'), (P6) or (P6'), wherein the hydrogenation is carried out carried out in at least one solvent chosen from the group consisting of $CH_2Cl_2$, toluene, ethyl acetate, THF, methanol, ethanol and isopropanol (especially preferred are toluene and isopropanol).

The hydrogenation is usually carried out at an elevated temperature (30-150° C.).

Therefore the present invention relates to a process (P8), which is process (P), (P1), (P1'), (P1"), (P1'''), (P1''''), (P2), (P2'), (P2"), (P3), (P3'), (P3"), (P4), (P5), (P5'), (P6), (P6'), (P7), (P7') or (P7"), wherein the hydrogenation is carried out carried out at an elevated temperature (30-150° C.).

It is also possible to reduce the compound of formula (I) selectively by a transfer hydrogenation process. In that case no $H_2$ gas needs to be added. As reductant any suitable hydrogen donor can be used, including secondary alcohols, such as isopropanol and formic acid, its salts or derivatives.

Therefore the present invention relates to a process (P9), which is process (P), (P1), (P1'), (P1"), (P1'''), (P1''''), (P2), (P2'), (P2"), (P3), (P3'), (P3") or (P4), wherein the hydrogenation is a transfer hydrogenation.

The following examples serve to illustrate the invention. If not otherwise stated the temperature is given in ° C.

EXAMPLES

General:

Transition metal precursors, reagent and solvents were obtained from commercial sources and used as received unless noted otherwise. GC analysis was carried out on an Agilent 7890B GC system with a HP-5 normal-phase silica column, using Helium as a carrier gas and dodecane as an internal standard. NMR spectra were recorded on a Bruker AV400, Bruker AV300 or Bruker Fourier300 NMR spectrometer. $^1H$ and $^{13}C$-NMR spectra were referenced w.r.t. the solvent signal. Chemical shifts are in ppm, coupling constants in Hz. HR-MS measurements were recorded on an Agilent 6210 Time-of-Flight LC/MS, peaks as listed correspond to the highest abundant peak and are of the expected isotope pattern.

Ligand Synthesis

Example 1: 2-(ethylthio)-N-((6-methylpyridin-2-yl)methyl)ethan-1-amine [Ligand of Formula (IVg)]

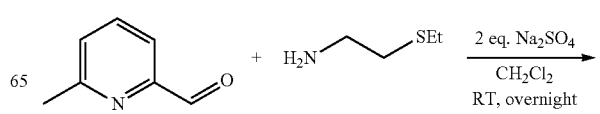

-continued

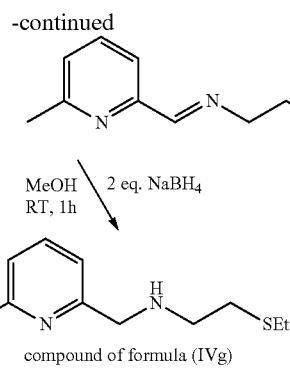

compound of formula (IVg)

6-methylpyridine-2-carboxaldehyde (3.0 g, 25 mmol) and 2-(Ethylthio)ethylamine (2.63 g, 2.8 mL, 25 mmol) were dissolved in $CH_2Cl_2$ (75 mL), then $Na_2SO_4$ (7.1 g, 50 mmol) was added. The suspension was stirred at room temperature overnight, filtered and the filter cake was washed with $CH_2Cl_2$. The combined volatiles were removed in vacuo, yielding 5.45 g of imine as brown oil, which was used directly in the following step without further purification. Therefore, the imine was dissolved in MeOH (50 mL) and $NaBH_4$ (1.9 g, 51 mmol) was added portionwise at 0° C. The mixture was stirred at room temperature for another hour, after which the solvent was removed in vacuo. Then $CH_2Cl_2$ (20 mL) and water (20 mL) were added. The aqueous layer was extracted with $CH_2Cl_2$ (three times 20 mL). The combined organic layers were washed with brine (20 mL) and dried over $Na_2SO_4$. Evaporating the solvent and drying in vacuo yielded 4.95 g (94%) of the ligand of formula (IVg) as an orange oil, which was directly used for complex synthesis.

$^1$H-NMR (300 MHz, $CDCl_3$): δ 7.45 (t, 1H, J=7.6, $CH_{arom}$), 7.07 (d, 1H, J=7.8, $CH_{arom}$), 6.96 (d, 1H, J=7.5, $CH_{arom}$), 3.84 (s, 2H), 2.80 (dt, 2H), 2.66 (dt, 2H), 2.48 (m, 5H), 1.23 (t, 3H, J=7.4) ppm.

$^{13}$C-NMR (75 MHz, $CDCl_3$): δ 158.9, 157.8, 136.5, 121.3, 118.9, 54.9, 48.2, 31.8, 25.6, 24.4 ppm.

HRMS (ESI+): calculated for $C_{11}H_{18}N_2S$: 210.1191; found 211.1265 (M+H), 233.1082 (M+Na).

Example 2: 2-(methylthio)-N-((pyridin-2-yl)methyl)ethan-1-amine [Ligand of Formula (IVa)]

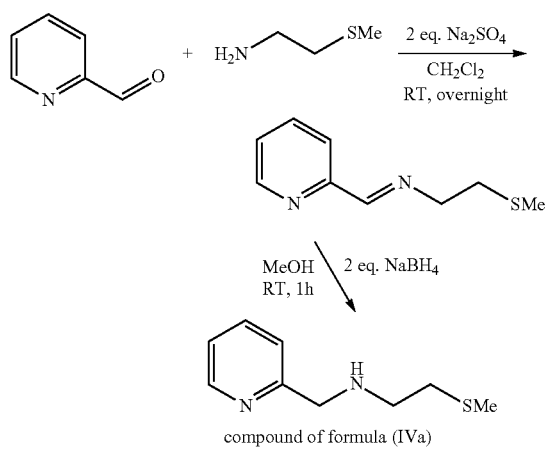

compound of formula (IVa)

The ligand of formula (IVa) was prepared in analogy to Example 1.

$^1$H NMR (300 MHz, $CD_2Cl_2$) δ 8.43 (ddd, 1H, J=4.9 Hz, J=1.8 Hz, J=0.9 Hz, $CH_{arom}$), 7.57 (td, 1H, J=7.7 Hz, J=1.8 Hz, $CH_{arom}$), 7.24 (d, 1H, J=7.8 Hz, $CH_{arom}$), 7.07 (dd, 1H, J=7.5 Hz, J=5.0.7 Hz, $CH_{arom}$), 3.81 (s, 2H), 2.75 (td, 2H, J=6.5 Hz, J=0.8 Hz, $CH_2$), 2.58 (td, 2H, J=6.5 Hz, J=0.6 Hz, $CH_2$), 1.99 (s, 3H, $CH_3$) ppm.

$^{13}$C NMR (75 MHz, $CD_2Cl_2$): δ 160.2, 149.1, 136.2, 121.9, 121.7, 54.8, 47.6, 34.4, 15.0 ppm.

HRMS (ESI+): calculated for $C_9H_{14}N_2S$: 182.0878 (M+H): 183.0950; found 183.0950 (M+H).

Example 3: 2-(ethylthio)-N-((pyridin-2-yl)methyl)ethan-1-amine [Ligand of Formula (IVb)]

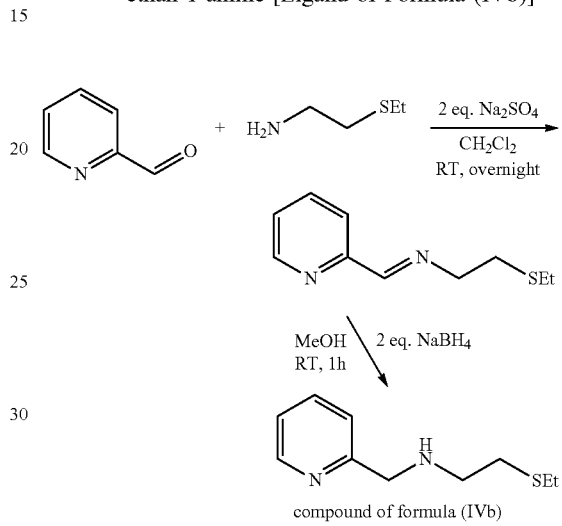

compound of formula (IVb)

The ligand of formula (IVb) was prepared according to Example 1.

$^1$H NMR (300 MHz, $CD_2Cl_2$): δ 8.51 (ddd, 1H, J=4.8 Hz, J=1.5 Hz, J=0.9 Hz, $CH_{arom}$), 7.64 (td, 1H, J=7.5 Hz, J=1.8 Hz, $CH_{arom}$), 7.32 (d, 1H, J=7.8 Hz, $CH_{arom}$), 7.19-7.12 (m, 1H, $CH_{arom}$), 3.88 (s, 2H, $CH_2$), 2.85-2.79 (m, 2H, $CH_2$), 2.72-2.66 (m, 2H, $CH_2$), 2.52 (q, 2H, J=7.5 Hz, $CH_2$), 2.09 (d, 1H, J=9.6 Hz, NH), 1.23 (t, 3H, J=7.4 Hz, $CH_3$) ppm.

$^{13}$C NMR (75 MHz, $CD_2Cl_2$): δ 161.6, 149.7, 136.8, 122.5, 122.3, 55.4, 48.9, 32.5, 26.2, 15.3 ppm.

HRMS (ESI+): calculated for $C_{10}H_{16}N_2S$: 196.1034; (M+H): 197.1107; (M+Na): 219.0926; found 197.1108 (M+H), 219.0929 (M+Na).

Example 4: 2-(ethylthio)-N-((6-methoxy-pyridin-2-yl)methyl)ethan-1-amine [Ligand of Formula (IVk)]

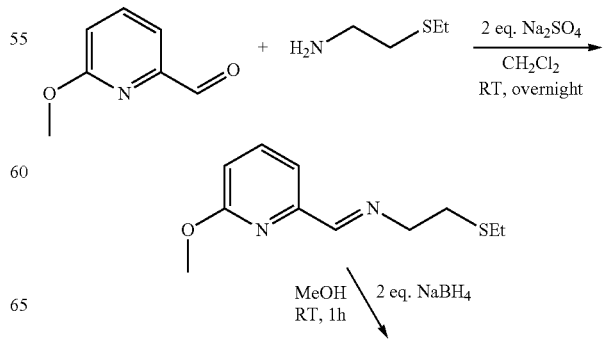

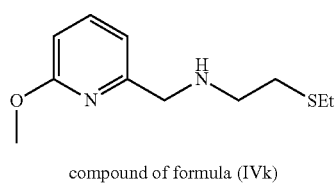

compound of formula (IVk)

The ligand of formula (IVk) was prepared according to Example 1 in a 84% yield.

$^1$H-NMR (300 MHz, CDCl$_3$): δ 7.54 (dd, 1H, J=8.1, J=7.4, CH$_{arom}$), 6.87 (d, 1H, J=7.2), 6.63 (d, 1H, J=8.1), 4.55 (s, NH), 3.92 (s, 3H), 3.90 (m, NH), 3.80 (s, 2H), 2.83 (t, 2H, J=6.5), 2.66 (t, 2H, J=6.5), 2.52 (t, 2H, J=7.5), 1.23 (t, 3H, J=7.2) ppm. $^{13}$C-NMR (75 MHz, CDCl$_3$): δ 163.8, 157.3, 138.8, 114.5, 108.7, 54.3, 53.2, 48.1, 32.0, 25.8, 14.8 ppm.

HRMS (ESI+): calculated for C$_{11}$H$_{18}$N$_2$OS: 227.1213 (M+H); found 227.1217 (M+H).

Example 5: 2-(ethylthio)-N-((quinolin-2-yl)methyl)ethan-1-amine [Ligand or Formula (IVl)]

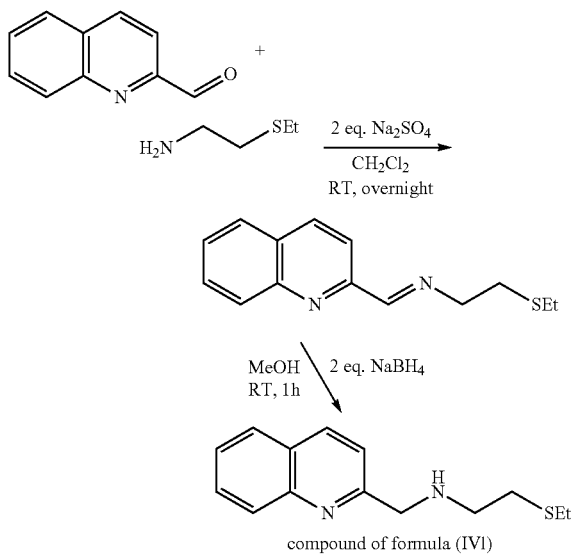

compound of formula (IVl)

The ligand of formula (IVl) was prepared according to Example 1 and purification by Kugelrohr distillation.

$^1$H NMR (300 MHz, CD$_2$Cl$_2$): δ 8.13 (d, 1H, J=8.4 Hz, CH$_{arom}$), 8.00 (d, 1H, J=8.7 Hz, CH$_{arom}$), 7.82 (dd, 1H, J=8.3 Hz, J=1.5 Hz, CH$_{arom}$), 7.69 (ddd, 3H, J=8.5 Hz, J=6.9 Hz, J=1.5 Hz, CH$_{arom}$), 7.55-7.45 (m, 2H, CH$_{arom}$), 4.08 (s, 2H, CH$_2$), 2.89 (td, 2H, J=6.8 Hz, J=1.2 Hz, CH$_2$), 2.73 (td, 2H, J=6.4 Hz, J=0.9 Hz, CH$_2$), 2.55 (q, 2H, J=7.4 Hz, CH$_2$), 2.14 (d, 1H, J=11.4 Hz, NH), 1.24 (t, 3H, J=7.4 Hz, CH$_3$) ppm.

$^{13}$C NMR (75 MHz, CD$_2$Cl$_2$): δ 161.5, 136.7, 129.8, 129.5, 128.1, 127.9, 126.5, 121.0, 56.0, 49.1, 32.6, 26.2, 15.29 ppm.

HRMS (ESI+): calculated for C$_{14}$H$_{18}$N$_2$S: 246.1191; (M+H): 247.1264; found 247.1267 (M+H).

Example 6: 2-(ethylthio)-N-(1-(pyridin-2-yl)ethyl)ethan-1-amine [Ligand or Formula (IVe)]

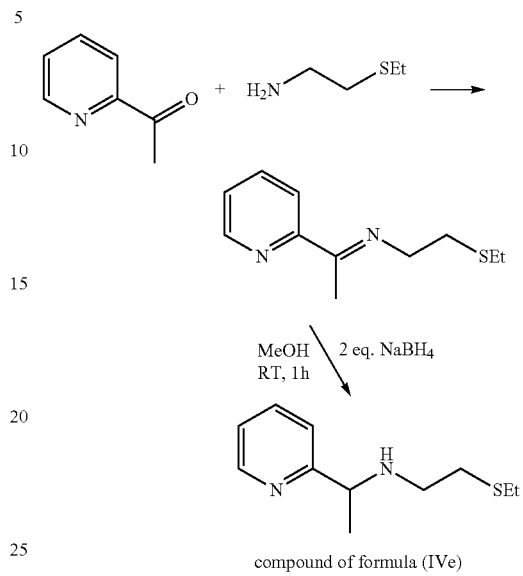

compound of formula (IVe)

The ligand of formula (IVe) was prepared according to Example 1 with imine formation performed in the presence of 5 mol % of p-toluenesulfonic acid in toluene under reflux conditions and purification by Kugelrohr distillation.

$^1$H NMR (300 MHz, CD$_2$Cl$_2$): δ 8.51 (ddd, 1H, J=4.8 Hz, J=1.9 Hz, J=1.0 Hz, CH$_{arom}$), 7.64 (td, 1H, J=7.6 Hz, J=1.8 Hz, CH$_{arom}$), 7.32 (dt, 1H, J=7.8 Hz, J=1.1 Hz, CH$_{arom}$), 7.14 (ddt, 1H, J=7.5 Hz, J=4.8 Hz, J=1.2 Hz, CH$_{arom}$), 3.84 (q, 1H, J=6.9 Hz, CH), 2.71-2.55 (m, 4H, CH$_2$), 2.47 (q, 2H, J=7.4 Hz, CH$_2$), 2.05 (d, 1H, J=39.3 Hz, NH), 1.34 (d, 3H, J=6.9 Hz, CH$_3$), 1.20 (d, 3H, J=7.5 Hz, CH$_3$) ppm.

$^{13}$C NMR (75 MHz, CD$_2$Cl$_2$): δ 165.4, 149.7, 136.9, 122.3, 121.4, 59.7, 47.1, 32.7, 26.1, 23.2, 15.2 ppm.

HRMS (ESI+): calculated for C$_{11}$H$_{18}$N$_2$S: 210.1191; (M+H), 211.1264; (M+Na): 233.1083; found 211.1265 (M+H), 233.1083 (M+Na).

Example 7: 2-(ethylthio)-N-methyl-N-(pyridin-2-ylmethyl)ethan-1-amine [Ligand or Formula (IVd)]

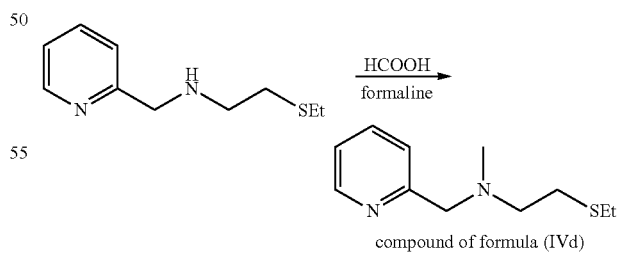

compound of formula (IVd)

2-(Ethylthio)-N-(pyridin-2-ylmethyl)ethan-1-amine (ligand of formula (IVb), 850 mg, 3.75 mmol), formalin (4 mL of 37% wt formaldehyde in water) and formic acid (4 mL) were stirred at 70° C. overnight. All volatiles were removed in vacuo and CH$_2$Cl$_2$ (10 mL) and saturated NaHCO$_3$ solution (10 mL) were added. The aqueous layer was extracted with CH$_2$Cl$_2$ (three times 10 mL). The combined organic layers were washed with brine (20 mL) and dried over Na$_2$SO$_4$. Removal of the solvent yielded 754 mg (3.59 mmol, 96%) of 2-(ethylthio)-N-methyl-N-(pyridin-2-ylm-ethyl)ethan-1-amine as an orange liquid (ρ=1.081 g cm$^{-3}$). The ligand of formula (IVb) was further purified by Kugel-rohr distillation.

$^1$H-NMR (300 MHz, CDCl$_3$): δ 8.46 (d, 1H, J=5.1, CH$_{arom}$), 7.58 (dt, 1H, J=7.8, J=1.8, CH$_{arom}$), 7.38 (d, 1H, J=7.8, CH$_{arom}$), 7.08 (ddd, 1H, J=7.5, J=4.8, J=1.2, CH$_{arom}$), 3.62 (s, 2H), 2.62 (s, 4H), 2.45 (q, 2H, J=7.4), 2.31 (s, 3H, N—CH$_3$), 1.17 (t, 3H, J=7.4) ppm.

$^{13}$C NMR (101 MHz, CDCl$_3$): δ 159.2, 149.0, 136.4, 123.1, 122.0, 63.6, 57.3, 56.9, 42.4, 31.9, 29.3, 26.1, 14.8 ppm.

HRMS (ESI+): calculated for C$_{11}$H$_{18}$N$_2$S: 210.1191; found 211.1265 (M+H), 233.1084 (M+Na).

Catalyst Synthesis

Example 8: Ru(6-MeNNS$^{Et}$)(PPh$_3$)Cl$_2$

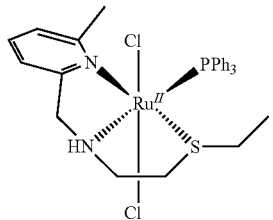

RuCl$_2$(PPh$_3$)$_3$ (1 g, 1.04 mmol) and the ligand of formula (IVg) (obtained from Example 1) (231.4 mg, 1.1 mmol) were placed in a 25 mL Schlenk tube under argon atmosphere, and dissolved in dry diglyme (2 mL). The reaction mixture was heated to 165° C. for 2 h, allowed to cool down to room temperature and stored at −18° C. to precipitate further overnight. Cold Et$_2$O (2 mL) was added while cooling with a dry ice/iso-propanol bath. The precipitate was filtrated by cannula, and washed with Et$_2$O (5 times 2 mL). The orange powder was dried in vacuo, affording 530 mg (79%) of Ru(6-MeNNS$^{Et}$)(PPh$_3$)Cl$_2$ as an orange powder. An equilibrium of two conformations of Ru(6-MeNNS$^{Et}$)(PPh$_3$)Cl$_2$ are existent in solution, delivering a doubled set of signals in NMR. For $^1$H-NMR only data of the major conformation is given due to overlapping signals.

$^1$H-NMR (300 MHz, CD$_2$Cl$_2$): δ 7.67-7.16 (m, 17H, CH$_{arom}$), 7.01 (d, 1H, J=7.8, CH$_{arom}$), 5.65 (m, 2H), 4.47 (m, 1H), 3.5 (m, 1H), 3.34 (m, 1H), 3.22 (d, 1H, J=11.1), 2.98 (m, 1H), 2.59 (m, 1H), 1.53 (m, 2H), 0.87 (t, 3H, J=7.5) ppm.

$^{31}$P-NMR (122 MHz, CD$_2$Cl$_2$): δ 48.8, 45.8 ppm.

HRMS (ESI+): calculated for C$_{29}$H$_{32}$Cl$_2$N$_2$PRuS (M+H): 644.0518; found 644.0518 (M+H), 667.0412 (M+Na).

Example 9: Ru(NNS$^{Me}$)(PPh$_3$)Cl$_2$

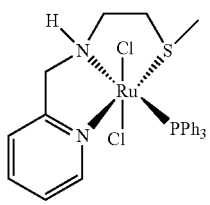

Ru(NNS$^{Me}$)(PPh$_3$)Cl$_2$ was prepared according to Example 8. An equilibrium of two conformations was obtained.

$^1$H-NMR (300 MHz, CD$_2$Cl$_2$): δ 8.47 (d, 1H, J=5.7), 7.72 (m, 1H), 7.56 (m, 6H), 7.32 (m, 10H), 6.86 (t, 1H, J=6.3), 5.45 (s, broad, 1H, NH), 5.20 (t, 1H, J=12.6), 4.38 (m, 1H), 3.41 (m, 2H), 3.26 (d, 1H, J=11.1), 2.55 (m, 1H), 1.50 (s, 3H).

$^{31}$P-NMR (122 MHz, CD$_2$Cl$_2$): δ 51.8, 50.7

HRMS (ESI+): calculated for C$_{27}$H$_{29}$Cl$_2$N$_2$PRuS: 616.0210 (M+); found 616.0197 (M+).

Example 10: Ru(NNS$^{Et}$)(PPh$_3$)Cl$_2$

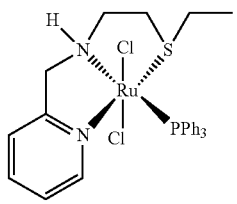

Ru(NNS$^{Et}$)(PPh$_3$)Cl$_2$ was prepared according to Example 8. An equilibrium of two conformations was obtained in 84% yield.

$^1$H-NMR (300 MHz, CD$_2$Cl$_2$): δ 8.45 (d, 1H, J=5.7), 7.72 (m, 1H), 7.57 (m, 6H), 7.34 (m, 10H), 6.86 (t, 1H, J=6.3), 5.49 (s, broad, 1H, NH), 5.22 (t, 1H, J=13.5), 4.40 (m, 1H), 3.47 (m, 2H), 3.36 (m, 1H), 2.80 (m, 1H), 2.52 (m, 1H), 1.27 (m, 2H), 1.19 (m, 1H), 0.95 (t, 3H, J=7.5)

$^{31}$P-NMR (122 MHz, CD$_2$Cl$_2$): δ 51.8, 50.7

HRMS (ESI+): calculated for C$_{28}$H$_{31}$Cl$_2$N$_2$PRuS: 630.0366 (M+); found 630.0388 (M+), 653.0270 (M+Na).

Example 11: Ru(6-MeONNS$^{Et}$)(PPh$_3$)Cl$_2$

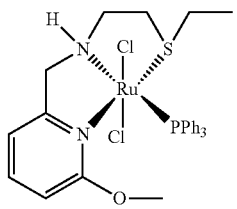

Ru(6-MeONNS$^{Et}$)(PPh$_3$)Cl$_2$ was prepared according to Example 8. An equilibrium of two conformations was obtained in 88% yield.

$^1$H-NMR (400 MHz, CD$_2$Cl$_2$): δ 7.94 (m, 2H), 7.65 (m, 2H), 7.42-7.14 (m, 12H), 7.07 (d, 1H, J=7.6), 6.56 (d, 1H, J=8.4), 5.56-5.36 (m, 2H), 4.46 (m, 1H), 3.50-3.19 (m, 2H), 3.21 (dd, 1H, J=11.0, J=2.2), 2.87 (m, 1H), 2.83 (s, 3H, twinned), 2.50 (m, 1H), 1.33 (m, 1H), 0.87 (t, 3H, twinned, overlapping)

$^{31}$P-NMR (122 MHz, CD$_2$Cl$_2$): δ 47.2, 45.9

HRMS (ESI+): calculated for C$_{29}$H$_{32}$Cl$_2$N$_2$OPRuS (M+H): 660.0468; found: 660.0469 (M+H), 683.0363 (M+Na).

Example 12: Ru(QuinNS$^{Et}$)(PPh$_3$)Cl$_2$

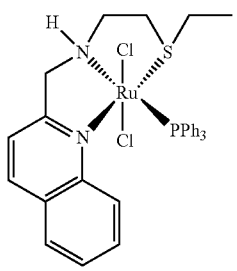

Ru(QuinNS$^{Et}$)(PPh$_3$)Cl$_2$ was prepared according to Example 8. An equilibrium of two conformations was obtained.

$^1$H-NMR (300 MHz, CD$_2$Cl$_2$): δ 8.12 (d, 2H, J=8.4), 7.74-6.66 (m, 19H), 5.90 (s, broad, NH), 5.74 (t, 1H, J=13.3), 4.72 (m, 1H), 3.58-3.40 (m, 3H), 3.05 (m, 1H), 2.72 (m, 1H), 1.66 (m, 1H), 0.95 (t, 3H, J=7.5)

$^{31}$P NMR (122 MHz, CD$_2$Cl$_2$): δ 48.90, 45.86

HRMS (ESI+): calcd. for C$_{32}$H$_{33}$Cl$_2$N$_2$PRuS: 680.0519 (M+); found 680.0500 (M+).

Example 13: Ru(N-Me-NS$^{Et}$)(PPh$_3$)Cl$_2$

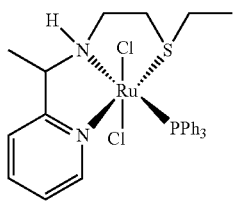

Ru(N-Me-NS$^{Et}$)(PPh$_3$)Cl$_2$ was prepared according to Example 8. An equilibrium of two conformations was obtained.

$^1$H-NMR (300 MHz, CD$_2$Cl$_2$): δ 8.53 (d, 1H, J=5.7), 7.72 (m, 1H), 7.57 (m, 6H), 7.33 (m, 10H), 6.85 (t, 1H, J=6.6), 5.35 (m, 1H), 4.93 (s, broad, NH), 3.68-3.31 (m, 3H), 2.81 (m, 1H), 2.53 (m, 1H), 1.80 (d, 3H, J=6.9), 1.25 (m, 1H), 0.97 (t, 3H, J=7.2) $^{31}$P NMR (122 MHz, CD$_2$Cl$_2$): δ 51.5, 50.3

HRMS (ESI+): calculated for C$_{29}$H$_{33}$Cl$_2$N$_2$PRuS: 644.0518 (M+); found 644.0513 (M+).

Example 14: Ru(NN$^{Me}$S$^{Et}$)(PPh$_3$)Cl$_2$

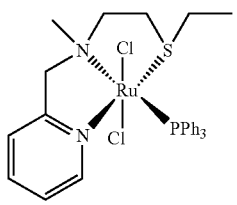

Ru(NN$^{Me}$S$^{Et}$)(PPh$_3$)Cl$_2$ was prepared according to Example 8. An equilibrium of two conformations was obtained in 54%.

$^1$H-NMR (300 MHz, CD$_2$Cl$_2$): δ 8.11 (d, 1H, J=5.7), 7.92 (m, 6H), 7.47 (dt, 1H, J=7.5, J=1.5), 7.30 (m, 10H), 6.56 (t, 1H, J=7.5), 5.67 (d, 1H, J=14.4), 3.87 (d, 1H, J=14.4), 3.15 (s, 3H), 2.86 (m, 1H), 2.70 (m, 1H), 2.30 (m, 2H), 0.74 (m, 1H), 0.67 (t, 3H, J=6.9), 0.42 (m, 1H)

$^{31}$P-NMR (122 MHz, CD$_2$Cl$_2$): δ 51.4, 50.4

HRMS (ESI+): calculated for C$_{29}$H$_{33}$Cl$_2$N$_2$PRuS: 644.0518 (M+); found 644.0505 (M+).

Hydrogenation Reactions

Example 15: Selective Hydrogenation of a Specific Ester

The compounds of formulae (A) were hydrogenated.

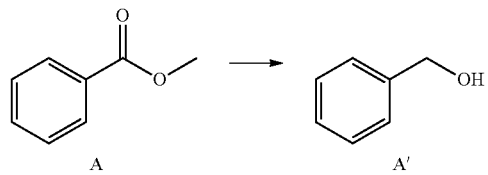

A    A'

4 mL glass reaction vials and stirring bars were dried overnight at 110° C., closed with PTFE/rubber septa, placed in a multiple reactor inlet suitable for a pressure vessel, and brought under argon atmosphere by three vacuum-argon cycles. With a syringe the reaction vessels were charged with the catalyst as stock solution in iPrOH (1 mL, 0.0005 mol/L, 0.05 mol %), followed by a solution of the compound A, in iPrOH (1 mL, 1 mol/L, 1 mmol). After that a solution of freshly sublimed base in THF (12.5 µL, 1 mol/L, 0.0125 mmol, 1.25 mol %) was added with a syringe. The reaction mixtures were transferred to an argon-filled pressure vessel, which was immediately flushed with three nitrogen and three hydrogen cycles, then pressurized to 30 bar hydrogen, heated to 80° C. and stirred for 16 h. After that the pressure vessel was cooled down to room temperature and depressurized. The reaction mixtures were filtered over silica and rinsed with ethanol (2 mL). The products are determined based on GC analysis retention time. The given values [%] are related to GC area %.

The results are summarized in the following table.

TABLE 1

HYDROGENATION OF THE COMPOUND OF FORMULA (A)

| Exp. | Cat. 0.05 mol % | Base 1-2 mol % | Conversion C [%] | Product Compound A' Y [%] | S [%] |
|---|---|---|---|---|---|
| 15a | Cat of Exp. 9 | KOtBu | 100 | 100 | 100 |
| 15b | Cat of Exp. 10 | KOtBu | 100 | 99 | 99 |
| 15c | Cat of Exp. 10 | LiOtBu | 100 | 99 | 99 |

Example 16

In a similar manner as described in Example 15 methyl hexanoate was hydrogenated to 1-hexanol. In this experiment the catalyst of Exp 9 was used and NaOtBu was used as base. The ratios between substrate base and catalyst were 262:29:1. The temperature was 100° C. and the hydrogen pressure 30 bar. After 16 h the solution was analysed and 1-hexanol was found in 43% yield.

Example 17

A 100 mL hastelloy autoclave with mechanical stirrer was charged with the catalyst of example 9 (3.3 mg, 0.005 mmol), methyl stearate (2.98 g, 10 mmol), 20 mL of toluene, and freshly sublimed KOtBu (7 mg, 0.0625 mmol, 1.25 mol %) under an argon atmosphere. The autoclave vessel was then pressurized to 30 bar hydrogen, heated to 100° C. and stirred for 16 hours. The pressure vessel was cooled down to room temperature and depressurized. Removal of the solvent in vacuo yielded 2.7 g of stearyl alcohol as an off-white flaky powder.

1H NMR (300 MHz, CDCl3): δ 3.69 (dt, 2H, J=6.6; J=5.4 Hz), 1.62 (m, 2H), 1.30 (m, 31H), 0.93 (t, 3H, J=6.3 Hz) ppm.

GC-MS (ESI-): single component, calculated for C18H38O: 270 (M); found 269 (M-H).

Example 18: Hydrogenation of Cinnamate Esters

A 100 mL hastelloy autoclave with mechanical stirrer was charged with the catalyst of example 9 (23 mg, 0.038 mmol, 0.25 mol %), substrate (15 mmol), 30 mL of toluene, freshly sublimed KOtBu (41 mg, 0.38 mmol, 2.5 mol %), and 1000 μl of anhydrous n-dodecane under an argon atmosphere. The autoclave vessel was flushed with nitrogen three times, and with hydrogen two times, then pressurized to 30 bar H2, heated to 40° C. and stirred for 4 hours. During the reaction time the pressure was kept at 30 bar $H_2$. The products are determined based on GC analysis retention time. The given values for conversion (C), yield (Y), and selectivity (S) [%] are mol % with regard to the initial cinnamyl ester amount, and corrected by n-dodecane. The results are summarized in the following table.

TABLE 2 hydrogenation of cinnamate esters

| Exp | Substrate | T [° C.] | t [h] | C [%] | S [%] | Y [%] |
|---|---|---|---|---|---|---|
| 18a | Methyl cinnamate | 40 | 4 | >99 | 90 | 90 |
| 18b | Isobutyl cinnamate | 40 | 4 | >99 | 95 | 95 |

Example 19: Hydrogenation of 5-methyldihydrofuran-2(3H)-one

The catalyst of example 9 (23 mg, 0.038 mmol, 0.25 mol %), 5-methyldihydrofuran-2(3H)-one (1.46 g, 15 mmol), 30 mL of toluene, and freshly sublimed KOtBu (41 mg, 0.38 mmol, 2.5 mol %) were reacted according to the method in Example 18. An amount of 25 mL of the reaction mixture was used for the product purification. Column chromatography yielded 1.399 g (92%) of pentane-1,4-diol.

Example 20: Hydrogenation of methyl cyclohex-1-ene-1-carboxylate

Methyl cyclohex-1-ene-1-carboxylate was hydrogenated according to Example 18. The reaction mixture was initially heated to 60° C. After stirring for 1 hour the vessel was allowed to cool down to 40° C. and was kept at this temperature under stirring for 5 hours. Column chromatography yielded 0.75 g (63%) of cyclohex-1-en-1-ylmethanol.

The invention claimed is:

1. A process of production of a compound of formula (II):

(II)

wherein
$R_1$ is an aromatic ring system which is unsubstituted or an aromatic ring system which is substituted; a heteroaromatic ring system which is unsubstituted or a heteroaromatic ring system which is substituted; an aliphatic ring system which is unsubstituted or an aliphatic ring system which is substituted; —$CH_3$; —$CH_2CH_3$; an unsubstituted $C_3$-$C_{22}$ alkyl group, which can be linear or branched and which can also be partially unsaturated; or a substituted $C_2$-$C_{22}$ alkyl group, which can be linear or branched and which can also be partially unsaturated, wherein the process comprises conducting a selective reduction of a compound of formula (I):

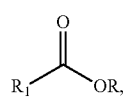

(I)

wherein
R is a linear $C_1$-$C_6$-alkyl group, which can be substituted; a branched $C_3$-$C_6$-alkyl group, which can be substituted or a benzyl group, which can be substituted, and
$R_1$ is an aromatic ring system which is unsubstituted or an aromatic ring system which is substituted; a heteroaromatic ring system which is unsubstituted or a heteroaromatic ring system which is substituted; an aliphatic ring system which is unsubstituted or an aliphatic ring system which is substituted; —$CH_3$; —$CH_2CH_3$; an unsubstituted $C_3$-$C_{22}$ alkyl group, which can be linear or branched and which can also be partially unsaturated; or a substituted $C_2$-$C_{22}$ alkyl group, which can be linear or branched and which can also be partially unsaturated, or
R and $R_1$ form together a 4 to 7 membered ring system, which can be substituted, and wherein
the selective reduction is carried out in the presence of at least one transition metal catalyst of formula (III):

$[M(L)(X)_a(L')_b]$ (III), wherein

M is a transition metal and
X is an anion, and
L' is a monodentate ligand, and
L is a tridentate ligand of formula (IV):

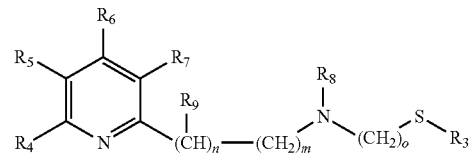

(IV)

wherein
$R_3$ is a linear $C_1$-$C_4$ alkyl group, which can be substituted; a branched $C_3$-$C_4$ alkyl group, which can be substituted; or a phenyl group, which can be substituted, $R_4$ is H; a linear $C_1$-$C_4$ alkyl group, which can be substituted; a branched $C_3$-$C_4$ alkyl group, which can be substituted; or $OC_1$-$C_2$alkyl, $R_5$ is H; a linear $C_1$-$C_4$ alkyl group, which can be substituted; a branched $C_3$-$C_4$ alkyl group, which can be substituted; or $OC_1$-$C_2$alkyl, or $R_4$ and $R_5$ form a $C_4$-$C_8$ ring system, which can be aliphatic or aromatic, and $R_6$ is H; a linear $C_1$-$C_4$ alkyl group, which can be substituted; a branched $C_3$-$C_4$ alkyl group, which can be substituted; or $OC_1$-$C_2$alkyl, $R_7$ is H; a linear $C_1$-$C_4$ alkyl group, which can be substituted; a branched $C_3$-$C_4$ alkyl group, which can be substituted; or $OC_1$-$C_2$alkyl, $R_8$ is H or a linear $C_1$-$C_4$ alkyl group, which can be substituted; a branched $C_3$-$C_4$ alkyl group, which can be substituted, $R_9$ is —$CH_3$ or —$CH_2CH_3$, m is 0, 1 or 2, and n is 0, 1 or 2, with the proviso that the sum of m+n is 1 or 2, o is 2 or 3, a is 0, 1, 2, or 3, and b is 0, 1, 2, or 3, with the proviso that the sum of a+b is 2, 3 or 4.

2. The process according to claim 1, wherein the process is carried out in the presence of at least one base.

3. The process according to claim 1, wherein the process is carried out in the presence of at least one base of formula (VIII):

wherein $M^1$ is an alkali metal.

4. The process according to claim 1, wherein the process is carried out in the presence of at least one base of formula (VIII'):

wherein $M^1$ is Li, Na or K.

5. The process according to claim 1, wherein the process is carried out in the presence of at least one base selected form the group consisting of KOtBu, NaOtBu and LiOtBu.

6. The process according to claim 1, wherein the catalyst is a compound of formula (III):

wherein

M is a transition metal selected from the group consisting of Os, Co, Ru and Fe, and X is a halogen anion, a carboxylate, borohydride, hydride, $BF_4^-$ or $PF_6^-$, and L' is a monodentate phosphine ligand, and L is a tridentate ligand of formula (IV):

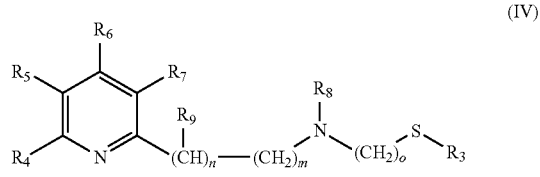

wherein $R_3$ is —$CH_3$ or —$CH_2CH_3$, $R_4$ is H; —$CH_3$; —$CH_2CH_3$; —$OCH_3$ or —$OCH_2CH_3$, and $R_5$ is H; —$CH_3$; —$CH_2CH_3$; —$OCH_3$ or —$OCH_2CH_3$, or $R_4$ and $R_5$ form a $C_4$-$C_8$ ring system, which can be aliphatic or aromatic, and $R_6$ is H; —$CH_3$; —$CH_2CH_3$; —$OCH_3$ or —$OCH_2CH_3$, $R_7$ is H; —$CH_3$; —$CH_2CH_3$; —$OCH_3$ or —$OCH_2CH_3$, $R_8$ is H; —$CH_3$ or —$CH_2CH_3$, $R_9$ is —$CH_3$ or —$CH_2CH_3$, m is 0, 1 or 2, and n is 0, 1 or 2, with the proviso that the sum of m+n is 1 or 2, o is 2 or 3, a is 0, 1, 2, or 3, and b is 0, 1, 2, or 3, with the proviso that the sum of a+b is 2 or 3.

7. The process according to claim 1, wherein the catalyst is a compound following catalysts of formula (III'):

wherein

M is Ru or Fe,

X is $Cl^-$,

L' is $PPh_3$, and

L is a tridentate ligand selected from the group consisting of the ligands of formulae (IVa)-(IVl):

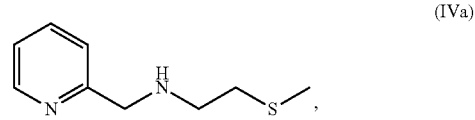

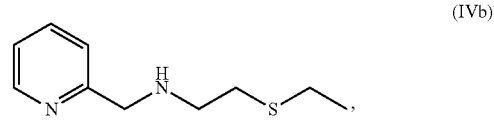

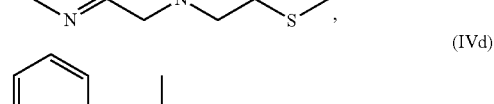

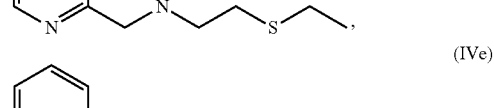

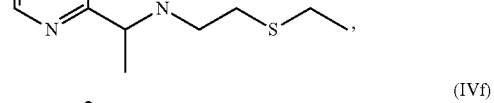

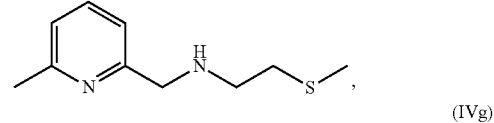

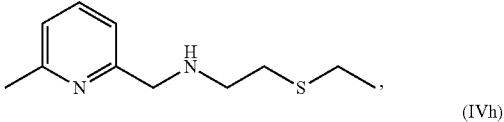

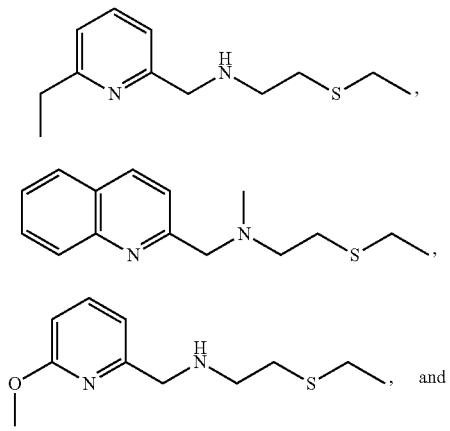

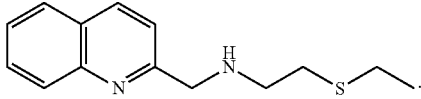

8. The process according to claim 1, wherein the catalyst of formula (III) is used in an amount of 0.001-0.5 mol-%, based on the number of moles of the compounds of formula (I).

9. The process according to claim 1, wherein the reduction is a transfer hydrogenation.

10. The process according to claim 1, wherein the process is carried out with $H_2$ gas.

11. The process according to claim 10, wherein the process is carried out at a pressure of 10-50 bar.

12. The process according to claim 1, wherein the process is carried out at a temperature of 30-150° C.

* * * * *